US009757039B2

(12) United States Patent
Lasser et al.

(10) Patent No.: US 9,757,039 B2
(45) Date of Patent: *Sep. 12, 2017

(54) FUNCTIONAL OPTICAL COHERENT IMAGING

(71) Applicant: ECOLE POLYTECHNIQUE FEDERALE DE LAUSANNE (EPFL), Lausanne (CH)

(72) Inventors: Theo Lasser, Denges (CH); Dimitri Van De Ville, Nyon (CH); Erica Martin-Williams, Pully (CH); Marcel Leutenegger, Göttingen (DE); Iwan Maerki, Yverdon-les-Bains (CH); Michael Friedrich, Lausanne (CH); Martin Villiger, Ecublens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 125 days.

This patent is subject to a terminal disclaimer.

(21) Appl. No.: 14/753,997

(22) Filed: Jun. 29, 2015

(65) Prior Publication Data
US 2016/0367145 A1 Dec. 22, 2016

Related U.S. Application Data

(63) Continuation of application No. 13/057,593, filed as application No. PCT/IB2008/052787 on Jul. 10, 2008, now Pat. No. 9,066,686.

(51) Int. Cl.
*A61B 6/00* (2006.01)
*A61B 5/00* (2006.01)
(Continued)

(52) U.S. Cl.
CPC .......... *A61B 5/0066* (2013.01); *A61B 3/1233* (2013.01); *A61B 5/0048* (2013.01);
(Continued)

(58) Field of Classification Search
CPC ..... A61B 3/102; A61B 3/1233; A61B 5/0048; A61B 5/0059; A61B 5/0066;
(Continued)

(56) References Cited

U.S. PATENT DOCUMENTS 4,862,894 A  9/1989 Fujii
5,267,016 A  11/1993 Meinzer et al.
(Continued)

FOREIGN PATENT DOCUMENTS

CN  101926644 A  12/2010
DE  10 2008 017 390 A1  10/2009
(Continued)

OTHER PUBLICATIONS

Schmeisser et al., "Modification of the Heidelberg retinal flowmeter to record pattern and flicker induced blood flow changes", Documenta Opthalmologica Kluwer Academic Publishers NL, vol. 106, No. 3, May 2003, pp. 257-263; XP002516500.
(Continued)

*Primary Examiner* — George Manuel
(74) *Attorney, Agent, or Firm* — Morrison & Foerster LLP

(57) ABSTRACT

A functional optical coherent imaging (fOCI) platform includes at least one active camera unit (ACU) having a coherent and/or a partially coherent light source, and means for spectral filtering and imaging a selected body area of interest; an image processing unit (IPU) for pre-processing data received from an ACU; at least one stimulation unit (STU) transmitting a stimulation to a subject; at least one body function reference measurement unit (BFMU); a cen-
(Continued)

tral clock and processing unit (CCU), with interconnections to the ACU, the IPU, the STU, for collecting pre-processed data from the IPU, stimuli from the STU body function reference data from the BFMU in a synchronized manner; a post-processing unit (statistical analysis unit, SAU); and an operator interface (HOD. A process for acquiring stimuli activated subject data includes aligning a body function unit at a subject and monitoring pre-selected body function; selecting a stimulus or stimuli; imaging a body area of interest; exerting one or a series of stimuli on the subject; imaging the body area of interest synchronous with said stimuli and the preselected body functions; and transferring said synchronized image, stimuli and body function data to a statistical analysis unit (SAU) and performing calculations to generate results pertaining to body functions.

12 Claims, 12 Drawing Sheets

(51) Int. Cl.
  *A61B 3/12* (2006.01)
  *A61B 5/02* (2006.01)
  *A61B 3/10* (2006.01)

(52) U.S. Cl.
  CPC ........ *A61B 5/0059* (2013.01); *A61B 5/02028* (2013.01); *A61B 5/726* (2013.01); *A61B 5/7278* (2013.01); *A61B 5/742* (2013.01); *A61B 3/102* (2013.01); *A61B 5/413* (2013.01); *A61B 5/7203* (2013.01)

(58) Field of Classification Search
  CPC ... A61B 5/02028; A61B 5/413; A61B 5/7203; A61B 5/726; A61B 5/7278; A61B 5/742
  See application file for complete search history.

(56) References Cited

U.S. PATENT DOCUMENTS

| | | | |
|---|---|---|---|
| 6,045,511 A | 4/2000 | Ott et al. | |
| 6,178,340 B1 | 1/2001 | Svetliza | |
| 6,263,227 B1 | 7/2001 | Boggett et al. | |
| 6,728,561 B2* | 4/2004 | Smith | A61B 3/12 382/128 |
| 6,970,729 B2 | 11/2005 | Hartmann | |
| 7,113,817 B1 | 9/2006 | Winchester, Jr. et al. | |
| 7,123,363 B2* | 10/2006 | Puttappa | A61B 5/14532 356/450 |
| 7,231,243 B2 | 6/2007 | Tearney et al. | |
| 7,519,212 B2 | 4/2009 | Brady et al. | |
| 8,298,521 B2 | 10/2012 | Schwartz et al. | |
| 8,480,579 B2 | 7/2013 | Serov et al. | |
| 9,066,686 B2 | 6/2015 | Lasser et al. | |
| 2002/0052551 A1 | 5/2002 | Sinclair et al. | |
| 2002/0082480 A1 | 6/2002 | Riff et al. | |
| 2003/0023153 A1 | 1/2003 | Izatt et al. | |
| 2003/0137669 A1 | 7/2003 | Rollins et al. | |
| 2004/0034294 A1 | 2/2004 | Kimball et al. | |
| 2004/0176701 A1 | 9/2004 | Fujii | |
| 2004/0225222 A1 | 11/2004 | Zeng et al. | |
| 2005/0187477 A1 | 8/2005 | Serov et al. | |
| 2005/0206583 A1 | 9/2005 | Lemelson et al. | |
| 2006/0064024 A1 | 3/2006 | Schnall | |
| 2007/0100245 A1 | 5/2007 | Kashima | |
| 2007/0139613 A1 | 6/2007 | Tanifuji et al. | |
| 2007/0188707 A1 | 8/2007 | Nanjo | |
| 2007/0225606 A1 | 9/2007 | Naghavi et al. | |
| 2007/0291277 A1 | 12/2007 | Everett et al. | |
| 2008/0021329 A1 | 1/2008 | Wood et al. | |
| 2008/0100612 A1 | 5/2008 | Dastmalchi et al. | |
| 2008/0241199 A1 | 10/2008 | Silverman | |
| 2008/0294047 A1 | 11/2008 | Kodama et al. | |
| 2009/0054788 A1 | 2/2009 | Hauger et al. | |
| 2010/0099992 A1 | 4/2010 | Holschneider et al. | |
| 2010/0113940 A1 | 5/2010 | Sen et al. | |
| 2010/0191541 A1 | 7/2010 | Prokoski | |
| 2011/0013002 A1 | 1/2011 | Thompson et al. | |
| 2011/0090325 A1 | 4/2011 | Hauger et al. | |
| 2011/0099031 A1 | 4/2011 | Nair | |
| 2012/0071765 A1 | 3/2012 | Chinnock | |
| 2012/0078113 A1 | 3/2012 | Whitestone et al. | |
| 2013/0172735 A1 | 7/2013 | Andre et al. | |
| 2013/0223705 A1 | 8/2013 | Ferguson, Jr. et al. | |
| 2013/0296715 A1 | 11/2013 | Lasser et al. | |
| 2015/0080742 A1 | 3/2015 | Andre et al. | |
| 2015/0198797 A1 | 7/2015 | Andre et al. | |
| 2016/0328848 A1 | 11/2016 | Andre et al. | |

FOREIGN PATENT DOCUMENTS

| | | |
|---|---|---|
| EP | 1 982 645 A1 | 10/2008 |
| JP | S63-214238 A | 9/1988 |
| JP | H11-142748 A | 5/1999 |
| JP | 2003-516795 A | 5/2003 |
| JP | 2003-527700 A | 9/2003 |
| JP | 2004-267308 A | 9/2004 |
| JP | 2005-515818 A | 6/2005 |
| JP | 2005-532393 A | 10/2005 |
| JP | 2006-180926 A | 7/2006 |
| JP | 2007-315827 A | 12/2007 |
| JP | 2008-142355 A | 6/2008 |
| JP | 2008-289870 A | 12/2008 |
| JP | 2010-532699 A | 10/2010 |
| JP | 2011-027895 A | 2/2011 |
| JP | 2012-113191 A | 6/2012 |
| WO | WO-03/063677 A1 | 8/2003 |
| WO | WO-2005/099572 A1 | 10/2005 |
| WO | WO-2005/099582 A1 | 10/2005 |
| WO | WO-2006/111836 A1 | 10/2006 |
| WO | WO-2006/111909 A1 | 10/2006 |
| WO | 20061121984 A2 | 11/2006 |
| WO | WO-2007/148073 A1 | 12/2007 |
| WO | WO-2009/028136 A1 | 3/2009 |
| WO | WO-2010/004365 A1 | 1/2010 |
| WO | WO-2011/084528 A1 | 7/2011 |
| WO | WO-2011/117779 A2 | 9/2011 |
| WO | WO-2011/117779 A3 | 9/2011 |
| WO | WO-2013/160861 A1 | 10/2013 |
| WO | WO-2014/009859 A2 | 1/2014 |
| WO | WO-2014/009859 A3 | 1/2014 |

OTHER PUBLICATIONS

Database Biosis [Online] Biosciences Information Service, Georg et al., "Flickering light increases retinal blood flow", vol. 22, No. 3, Jun. 2002, pp. 336-343.
Jeong et al., "Functional optical coherence imaging of tumor response to a metabolic electron transport inhibitor", Proceedings of the SPIE, vol. 6079, No. 1, Feb. 2006, pp. 60790K-1-60790K-8.
International Preliminary Report on Patentability (IPRP) (Chapter I) for PCT/IB2008/052787, issued Jan. 11, 2011.
Written Opinion for PCT/IB2008/052787, mailed Mar. 24, 2009.
Briers, J.D. (Nov. 2001). "Laser Doppler, Speckle and Related Techniques for Blood Perfusion Mapping and Imaging," *Physiol. Meas.* 22(4):R35-R66.
Dyck, R.H. et al. (1968). "Integrated Arrays of Silicon Photodetectors for Image Sensing," *IEEE Transactions on Electron Devices* 15(4):196-202.
Jones, P.B. et al. (Jul.-Aug. 2008) "Simultaneous Multispectral Reflectance Imaging and Laser Speckle Flowmetry of Cerebral Blood Flow and Oxygen Metabolism in Focal Celebral Ischemia," *J. Biomed Opt.* 13(4):04407, twenty three pages.
Kalchenko, V. et al. (Feb. 10, 2001). "Multi-modal Diagnostic Approach for Functional Imaging of Tumor Vascular Network and Blood Microcirculation," *Proc. Of SPIE* 7898(1):1-7.
Leutenegger, M. et al. (May 9, 2011). "Real-Time Full Field Laser Doppler Imaging," *Biomedical Optics Express* 2(6).1470-1477.

(56) References Cited

OTHER PUBLICATIONS

Senarathna, J. et al. (Jan. 28, 2013). "Laser Speckle Contrast Imaging: Theory, Instrumentation, and Application," *IEEE Reviews in Biomedical Engineering* 6:99-110.
Serov, A. et al. (Oct. 3, 2001). "Speckles in Laser Doppler Blood Flowmetry," *Proceedings of the SPIE, SPIE* vol. 4242:306-318.
Serov, A. (2002). "Novel Instruments for Remote and Direct-Contact Laser Doppler Perfusion Imaging and Monitoring," Ph.D. Thesis, University of Twente, 128 pages.
Sun, X. et al. (May 14, 2011). "Simultaneous Monitoring of Intracellular PH Changes and Hemodynamic Response During Cortical Spreading Depression by Fluorescence-Corrected Multimodal Optical Imaging," *Neuroimage* 57(3):873-884.
Canadian Office Action dated Nov. 10, 2016 for Canadian Patent Application No. 2,914,780 filed on Jul. 10, 2012, four pages.
Canadian Office Action dated Oct. 12, 2016 for Canadian Application No. 2,909,914 filed on Apr. 25, 2013, four pages.
European Communication pursuant to Article 94(3) EPC dated Nov. 25, 2016 for European Application No. 08789265.9, filed on Feb. 8, 2011, five pages.
European Office Action dated Aug. 19, 2008, for EP Application No. 06 744 526.2, filed on Apr. 20, 2006, three pages.
European Office Action dated Dec. 4, 2012, for EP Application No. 06 744 526.2, filed on Apr. 20, 2006, four pages.
European Office Action dated Jul. 1, 2010, for EP Application No. 06 744 526.2, filed on Apr. 20, 2006, five pages.
International Search and Written Opinion dated Jul. 15, 2016 for PCT Application No. PCT/CA2016/050526, filed on May 6, 2016, eight pages.
International Search Report dated Aug. 14, 2006, for PCT Patent Application No. PCT/IB2006/000940, filed on Apr. 20, 2006, three pages.
International Search Report dated Aug. 14, 2006, for PCT Patent Application No. PCT/IB2006/051167, filed on Apr. 13, 2006, three pages.
International Search Report dated Jan. 3, 2014, for PCT Application No. PCT/IB2013/055517, filed on Jul. 5, 2013, six pages.
International Search Report dated Mar. 24, 2009, for PCT Application No. PCT/IB2008/052787, filed on Jul. 10, 2008, five pages.
International Search Report dated Nov. 23, 2011, for PCT Application No. PCT/IB2011/051098, filed on Mar. 16, 2011, seven pages.
International Search Report dated Sep. 11, 2013, for PCT Application No. PCT/IB2013/053271, filed on Apr. 25, 2013, four pages.
Japanese Office Action dated Feb. 1, 2016, for Japanese Patent Application No. 2015-521112, filed Jul. 5, 2013, twelve pages.
Japanese Office Action dated Oct. 30, 2015, for Japanese Patent Application No. 2015-507652, filed on Apr. 25, 2013, seven pages.
U.S. Final Office Action dated Apr. 4, 2016, for U.S. Appl. No. 13/636,268, filed Mar. 4, 2013, thirteen pages.
U.S. Final Office Action dated Aug. 18, 2011, for U.S. Appl. No. 11/912,224, filed Oct. 22, 2007, five pages.
U.S. Final Office Action dated Aug. 23, 2013, for U.S. Appl. No. 13/057,593, filed Mar. 21, 2011, fourteen pages.
U.S. Final Office Action dated Dec. 16, 2016 for U.S. Appl. No. 13/935,947, filed Jul. 5, 2013, twenty three pages.
U.S. Final Office Action dated Feb. 20, 2015, for U.S. Appl. No. 13/636,268, filed Mar. 4, 2013, seventeen pages.
U.S. Final Office Action dated Nov. 29, 2012, for U.S. Appl. No. 11/912,224, filed Oct. 22, 2007, eight pages.
U.S. Final Office Action dated Oct. 6, 2015, for U.S. Appl. No. 13/935,947, filed Jul. 5, 2013, fifteen pages.
U.S. Final Office Action dated Sep. 26, 2016, for U.S. Appl. No. 13/636,268, filed Mar. 4, 2013, fifteen pages.
U.S. Non Final Office Action dated Jan. 13, 2017 for U.S. Appl. No. 14/397,290, filed Oct. 27, 2014, thirteen pages.
U.S. Non-Final Office Action dated Apr. 29, 2016, for U.S. Appl. No. 13/935,947, filed Jul. 5, 2013, twenty pages.
U.S. Non-Final Office Action dated Aug. 11, 2014, for U.S. Appl. No. 13/057,593, filed Mar. 21, 2011, nineteen pages.
U.S. Non-Final Office Action dated Dec. 17, 2012, for U.S. Appl. No. 13/057,593, filed Mar. 21, 2011, fourteen pages.
U.S. Non-Final Office Action dated Jan. 16, 2015, for U.S. Appl. No. 13/935,947, filed Jul. 5, 2013, seven pages.
U.S. Non-Final Office Action dated Mar. 14, 2012, for U.S. Appl. No. 11/912,224, filed Oct. 22, 2007, seven pages.
U.S. Non-Final Office Action dated Mar. 8, 2011, for U.S. Appl. No. 11/912,224, filed Oct. 22, 2007, nine pages.
U.S. Non-Final Office Action dated Nov. 10, 2016, for U.S. Appl. No. 14/413,106, filed Jan. 6, 2015, twelve pages.
U.S. Non-Final Office Action dated Nov. 3, 2015, for U.S. Appl. No. 13/636,268, filed Mar. 4, 2013, fourteen pages.
U.S. Non-Final Office Action dated Sep. 29, 2014, for U.S. Appl. No. 13/636,268, filed Mar. 4, 2013, ten pages.
U.S. Notice of Allowance dated Feb. 27, 2015, for U.S. Appl. No. 13/057,593, filed Mar. 21, 2011, eight pages.
U.S. Notice of Allowance dated May 9, 2013, for U.S. Appl. No. 11/912,224, filed Oct. 22, 2007, six pages.
Written Opinion of the International Searching Authority dated Aug. 14, 2006, for PCT Patent Application No. PCT/IB2006/000940, filed on Apr. 20, 2006, seven pages.
Written Opinion of the International Searching Authority dated Aug. 14, 2006, for PCT Patent Application No. PCT/IB2006/051167, filed on Apr. 13, 2006, seven pages.
Written Opinion of the International Searching Authority dated Sep. 11, 2013, for PCT Application No. PCT/IB2013/053271, filed on Apr. 25, 2013, seven pages.
Written Opinion of the International Searching Authority dated Nov. 23, 2011, for PCT Application No. PCT/IB2011/051098, filed on Mar. 16, 2011, ten pages.
Written Opinion of the International Searching Authority dated Jan. 3, 2014, for PCT Application No. PCT/IB2013/055517, filed on Jul. 5, 2013, ten pages.
Michelson, G. et al. (2002). "Flickering Light Increases Retinal Blood Flow," *Retina* 22(3):336-343, full copy, eight pages.

* cited by examiner

FUNCTIONAL OPTICAL COHERENT IMAGING

CROSS-REFERENCE TO RELATED APPLICATIONS

This application is a continuation of U.S. patent application Ser. No. 13/057,593, filed Mar. 21, 2011, pending, which is a National Phase of PCT Application No. PCT/IB2008/052787, filed Jul. 10, 2008.

The present invention relates to a functional optical coherent imaging (fOCI) platform as well as a process for acquiring stimuli activated subject data.

DEFINITIONS

In the description the following terms will be used and for which we want to give some definitions.

"Source" is used to mean any source of electromagnetic radiation, preferably a coherent source with sufficient modal stability and a sufficiently long coherence length.

"Detector" is used herein to mean any device capable of measuring energy in an electromagnetic signal as a function of wavelength. A detector array means a plurality of detectors. In general the preferred detector arrays used in this disclosure have their optimal sensitivity in the wavelength range of the used source. The detectors can either be one-, multi-dimensional or line arrays, depending on the optical setup and the optical scan system. In the predominantly used wavelength range of around 800 nm, CMOS detectors have currently the best performance with respect to sensitivity and read out speed. However, current detector technology does not provide CMOS detectors that operate beyond the 1000 nm region. New detector technologies as for example GeSi detectors allow an extension of the detection range beyond 1000 nm and are included in this disclosure.

"Reflector" is used herein to mean any device capable of reflecting an electromagnetic signal. Thus, "reflector" can be used to mean a mirror, an abrupt change in an index of refraction, an auto-reflecting prism as well as a periodically spaced array structure such as a Bragg reflector. Applicants note that the terms "signal", "beam" and "light" are used in a synonymously manner, for including all forms of electromagnetic radiation suitable for use in imaging systems. It is also understood, that for the purposes of this disclosure, the term "optical" is to pertain to all wavelength ranges of electromagnetic radiation, and preferably pertains to the range of 100 nanometers to 30 micrometers.

"Stimulation" is used herein to mean any physical excitation of various natures as for example an optical, acoustical, electrical, thermal or chemical signal, or images, words and phrases (and/or pictures or representation of objects awaiting naming or recognition by the subject, or patterns), which induce by means of the subjects perception or sensory system a response by the subject, mainly a response expressed across a change of flow properties or a dynamic change of the microcirculation. It is important to distinguish between "external" stimulation and "internal" stimulation. Quite obviously, external stimulation is for example an external acoustic signal (for example bell ringing, words, music etc.), whereas as an example for internal stimulation would be the reading of a written piece of music, and the subject singing the melody, i.e. here the reading of music corresponds to an external stimulation and the internal stimulation the subject singing the melody. As internal stimulation, we also consider self-induced physiological stimuli e.g. holding ones breathe, clamp, and drug/pharmaceutical agent reactions.

"Body function" is used herein to mean any physiological process and in particular physiological process associated with blood flow and microcirculation happening without any internal or external stimulus. For example, the cardiovascular system and the linked microcirculation system receive the support of erythrocytes by the periodic heart pumping. This more or less periodical changing flow pattern is seen as a signal contribution in the functional fOCI-maps, often with dominant amplitude when compared to microcirculation responses due to stimuli. Breathing, vasomotion, saccadic movements, myogenic and neurogenic activities are additional body functions, which may overlay the stimulus response.

"Body area of interest" is used herein to mean areas which are observed by at least one active camera unit. As is obvious, the body area of interest can consist of different sub-areas of the subject which are captured by one or several ACUs, or may consist of different sub-areas which are observed with different types of ACU's.

"Channel" is used herein to mean any separate signal which is either observed or measured by an Active Camera Unit or the Body Function Reference Measurement Unit, or generated by the Stimulation Unit. All channels inputs are registered in a synchronized manner in order to be further processed by different fOCI sub-units.

"Flow maps" is used herein to mean any digital data, where functional parameters, calculated parameters or even measured data are represented as a functional image i.e. each x-y coordinate is associated to a functional value at this x-y coordinate.

"fOCI maps" is used herein to mean any digital data, where "flow maps" have been used as input for further statistical analysis. Associated to these fOCI maps can be the extraction of characteristic patterns or numbers for preparing or assisting the diagnostic result.

"Subject" is used herein to mean any patient for medical diagnosis. Nevertheless, the fOCI system can be used for animal and plant imaging as well. As it is obvious for those skilled in the art, fOCI imaging can be applied to animals as, i.e. to the measurement of animals, in particular small animals and even biomaterial.

"Diagnostic value" means herein at least one parameter extracted by any algorithm either from raw data, or pre-processed data, or post-processed data or any combination thereof. These parameters can be associated or related to a disease (based on an optional clinical study of representative subject group of healthy subjects against a disease group).

BACKGROUND OF THE INVENTION

The human body and in particular its regulation system continuously regulates the whole metabolism with respect to internal demands (oxygen, nutrition etc.) or external physical conditions and changes (temperature, humidity, etc.) or physical or intellectual efforts (physical working, sport, movements, intellectual work etc.) and all kind of threats (bacterial, viral etc.) including pathological disorders. Many of these regulation mechanisms act in a characteristic way on blood flow and/or the microcirculation and/or its regulation mechanisms. Therefore, the microcirculation and more precisely the associated hemodynamic response can be considered as an indirect indicator of body regulation actions. Stimuli, external or internal induce changes in the microcirculation or more precisely changes in the hemodynamic response. The same is in general also valid for all living beings, animals or even plants (where instead of hemodynamic response the plant perfusion can be monitored). Therefore, many regulation mechanisms in living beings can be partly monitored via the indirect response of the hemodynamic system or via changes in blood concentration and/or perfusion. As the regulation system reacts to external stimuli, an associated hemodynamic response can be used as an indicator for normal or abnormal response of the regulation system. Similar functional aspects are widely known in functional magnetic resonance imaging (fMRI).

Functional Optical Coherent Imaging (fOCI) is based on a non-contact imaging modality utilizing, to a large extent, the physical properties and in particular the coherence properties of light. This imaging modality integrates new and ultrafast detector technology, combined with an appropriate coherent light source and an image processing unit for extracting the flow characteristics of the observed body area of interest. Thereby, it allows for the diagnosis, or observation of multiple diseases and disorders such as peripheral vascular diseases, skin irritations, diabetes, burns, organ transplants, tissue grafts and even functional brain imaging. This method is in particular non-invasive because it involves no physical contact; therefore risk of infection and discomfort are greatly avoided.

As a sub-class of these optical coherent imaging methods, but not limited to them, there exists Laser Doppler Imaging (LDI), Laser Doppler Spectroscopic Imaging (LDSI), Laser Speckle Imaging (LSI), and Optical Coherence Tomography (OCT) which will all be described hereafter.

Laser Doppler Imaging (LDI) is a coherent imaging technique that allows the imaging of moving particles, e.g. blood flow or red blood cells, with good discrimination between perfusion, flow velocities and the concentration of the moving particles. It has made great progress during the last two decades from the initial proposals based on a scanning instrument towards a state of the art biomedical instrument, mainly due to a parallel imaging instrument based on a fast CMOS array of photo detectors.

The underlying concept is based on the fact that the back-reflected light from a biological sample or tissue or organ illuminated with a coherent light source consists of the superposition of two components: the first from the non-moving, static particles (e.g. the tissue) and the second from the moving, dynamic particles (e.g. the cells in the blood). The intensity fluctuations of this superposition encode the aforementioned flow information which can be extracted by sampling the fluctuations at a sufficiently high frequency and by applying appropriate signal analysis.

Current state of the art Laser Doppler Imaging techniques are disclosed in the three following patents and patent application, respectively, as well as in the publications "Serov A., Lasser T., High-speed laser Doppler perfusion imaging using an integrating CMOS image sensor, Optics Express 13#17: 6416-6428, Aug. 2005" and "Serov A., Steinacher B., Lasser T., Full-field laser Doppler perfusion imaging and monitoring with an intelligent CMOS camera, Optics Express 13#10: 3681-3689, May 2005".

In U.S. Pat. No. 6,263,227 there is described an apparatus for imaging micro vascular blood flow. The concept of using a 1D or 2D matrix of conventional photo detectors is described. The imager can work in two modes—scanning or static. In the scanning mode, a laser line is projected on the area of interest. The signals from the illuminated areas are detected by a 1D matrix of photo detectors. By scanning the illuminating laser light over the area of interest, a 2D perfusion map is obtained. In the static mode the whole area of interest is illuminated by an expanded laser beam or by light exiting an optical fiber. The Doppler signal is measured by a 2D matrix of photo detectors. Each photo detector has its own electronics for signal processing. A CCD camera is used to observe the object of interest. The perfusion maps are superimposed on the photographic image obtained with the CCD.

Laser Doppler perfusion imaging with a plurality of beams is known from the patent application WO03063677. Here, a structured illumination is used for illuminating a plurality of points or an area of interest. The Doppler signal from the illuminated areas is detected with a non-integrating random access high pixel readout rate image sensor. This single CMOS image sensor is used for detecting the Doppler signal and to obtain a photographic image of the object of interest.

The publication document WO06111836 describes an instrument and method for high-speed perfusion imaging. In contrast to both previously cited patents, the instrument described here uses integrating detectors which allow the signal to noise ratio to be improved compared to measurements with non-integrating detectors. Further, full field homogeneous illumination increases both resolution and read-out speed and makes it possible to combine LDI with speckle imaging, thus extracting more information.

Laser Doppler Spectroscopic Imaging (LDSI) is extending Laser Doppler Imaging (LDI) by making use of multi-wavelength illumination of the sample for gaining concentration information of specific molecules and compounds. The underlying LDI method makes it possible to achieve good discrimination between the concentration of the flowing molecules or compounds in the blood and the non-flowing molecules and compounds of the tissue. A prominent example of this method is the imaging of the oxy-deoxy-hemoglobin ratio which is possible with a two-wavelength illumination at 800 nm (e.g. the isobestic point) and 700 nm (providing an order of magnitude difference in absorption between the oxy- and the deoxy-state).

Laser Speckle Contrast Imaging (LSI) is as LDI a full-field flow imaging technique. The advantage of this approach is a fast image acquisition which is achieved at the expense of spatial and temporal resolution. This technique is exploited for flow measurements; however the acquired signal does not permit a discrimination between concentration and speed of the moving particles. Both said parameters influence the system response in the same manner; therefore the information content is different when compared with LDI. In addition, the system response is not linear with velocity since a finite camera integration time influences the measurement. A review of LSI can be found in the publication "Briers J. D., Laser Doppler, speckle and related techniques for blood perfusion mapping and imaging, Physiol. Meas. 22, R35-R66, 2001".

The LSI system obtains flow-related information by measuring the contrast of the image speckles formed by the detected laser light. If the sample consists of, or contains moving particles, e.g. blood cells, the speckle pattern fluctuates. The measured contrast is related to the flow parameters (such as speed and concentration of moving particles) of the investigated object. The contrast value is estimated for a certain integration time (exposure time) of the sensor. The faster the speckle pattern fluctuations, the lower the contrast value measured at a given exposure time. The control unit defines the exposure time of the image sensor to determine the range of the measured flow-related data related to the image contrast in LSI mode. Here, the integration time defines the range of measured speeds. The use of integrating image detectors is mandatory. Until now only the use of CCD type image sensors was reported for the technique.

Optical Coherence Tomography (OCT) represents an additional imaging modality (see for example "Saleh B. E. A., Teich M. C., Fundamentals of Photonics, Wiley & Sons Inc, New York, $2^{nd}$ Edition 2006, ISBN 978-0-471-35832-9"), from which flow data and in particular blood flow can be extracted from the acquired tomograms. A particular technique represents resonant Doppler flow imaging based on an interferometric imaging concept, where blood flow data is acquired via a path length modulation in the reference arm. This technique is disclosed for example in the documents WO2007085992; WO2006100544; EP1872084.

The hemodynamic mechanisms, which are well known in various medical fields and in particular in functional magnetic resonance imaging (fMRI), occur at timescales of from ~10 ms to several seconds or in a frequency range of 0.01-100 Hz. Over this timescale or frequency range, several natural body functions are overlaid masking the small changes of the hemodynamic system in response to the stimuli. The most important hemodynamic signals are the cardiac cycle, the natural heart beating driving the blood circulation. In addition, breathing as well as numerous other periodic components such as vasomotion are present and contribute strongly to the total signal observed. Overall, these natural functions are often stronger than the induced hemodynamic changes in response to the stimuli. In all mentioned optical coherent imaging modalities, but not limited thereto, these small changes are often not seen in the direct perfusion, speed or concentration maps. Even if seen, they are mostly not accessible for a quantitative evaluation and finally for a medical diagnosis and therefore have to be brought out by appropriate statistical analysis.

SUMMARY OF THE INVENTION

The invention disclosed here relates to Functional Optical Coherent Imaging (fOCI), a method using coherent illumination to visualize and analyze the response of the microcirculatory system to various predetermined stimuli applied to the subject by an integrated stimulation unit.

As set out already in section Background of the invention, several optical methods exist for imaging microcirculation, however they suffer from various limitations the most significant of which is the difficulty they experience in distinguishing sufficiently the signal of interest from all the other information acquired.

It is therefore an object of the current invention, fOCI, to overcome this specific limitation and this it achieves by combining within the Function Optical Coherent Imaging Platform; at least one active camera unit (ACU), an image processing unit (IPU), at least one stimulation unit (STU), at least one body function reference measurement unit (BFMU) and a central clock and processing unit (CCU) with a post-processing unit (SAU) and an operator interface (HOI). The hardware is accompanied by a process for acquiring stimuli activated subject data, this comprises: aligning a body function unit at a subject and monitoring pre-selected body function; selecting a stimulus or stimuli; imaging a body area of interest; exerting one or a series of stimuli on the subject; imaging the body area of interest synchronously with said stimuli and the preselected body functions; and transferring said synchronized image, stimuli and body function data to a statistical analysis unit (SAU) and performing calculations to produce results pertaining to body functions.

Further the invention discloses a process for acquiring stimuli activated subject data comprising the steps of aligning a body function unit at a subject and monitoring preselected body function; selecting a stimulus or stimuli; imaging a body area of interest; exerting one or a series of stimuli on the subject; imaging the body area of interest synchronously with said stimuli and the preselected body functions; and transferring said synchronized image, stimuli and body function data to a statistical analysis unit (SAU) and performing calculations to generate results pertaining to body functions.

With a fOCI-platform and a process for acquiring stimuli activated subject data according to the invention, a solution for the mentioned problems and/or limitations, i.e. the robust and reliable extraction of the hemodynamic response to stimuli in order to deliver diagnostic values of interest is proposed.

Functional Optical Coherent Imaging (fOCI) is a method for imaging the response to internal and/or external stimuli of hemodynamics/microcirculation and of blood flow properties. These changes in blood-flow are often measurable by optical methods such as Doppler shift, speckle dynamics and other contrast mechanisms. Flow dynamics, in particular blood flow, cause dynamic changes of the local complex index of refraction, in polarization properties or local dynamic changes in the fluorescence response (fluorescence intensity, lifetime, anisotropy), which allow the extraction of information on local flow properties and to present this functional information as parameter maps.

According to the invention all this is made possible with a sole system concept/platform and associated processes which enhance and improve the signal to noise ratio of for example classical optical coherent blood-flow imaging by statistical analysis. Thereby, the stimulation-induced response can be extracted from the responses caused by inherent body functions such as heart beat, breathing and vasomotion which are accessible and quantifiable as well. By coupling with a multi-wavelength illumination, constituents of blood differing in their absorption or fluorescence properties as for example the oxy-deoxy-hemoglobin ratio can be imaged. In addition, by proper filtering, the functional response across fluorescent parameters (intensity, lifetime etc.) can be mapped.

An advantage of the invention is that a total instrument platform is described, which overcomes the aforementioned limitations and which allows the extraction with high spatial resolution and good statistical confidence of the so-called fOCI maps as a result of a herein disclosed statistical analysis representing the locally enhanced microcirculation in response to internal or external stimuli.

According to the invention an overlay of the results of the statistical analysis is possible i.e. the so-called t-values over the conventional digitized image showing the locally enhanced hemodynamic response. This statistical test is by no means the only statistical test procedure—more statistical tests are known by those skilled in the art.

Further, according to the invention it becomes possible to build a general stimuli unit which allows the emission of stimulus signals (optical, acoustical, electrical, images etc.) and/or pictures or representations of objects (to be named) and to monitor precisely the time trace of these stimuli for further processing in the processing unit.

Also optical measuring means are disclosed for the monitoring of spectroscopic metabolic signatures as for example oxy-deoxy hemoglobin monitoring, where the concentration measurements are based on Laser Doppler imaging and deduced concentration measurements.

One aspect of the invention is to monitor metabolic signatures based on endogenous or exogenous fluorescence imaging, where specific bio-molecules are monitored based on their fluorescent signatures and further combined with additional flow maps and processed based on statistical analysis for final fOCI-maps and diagnostic purposes.

With a method according to the invention it is of great biomedical significance to provide a whole body area network, where at least two distinct body areas of interest are synchronously imaged and processed for the extraction of so-called phase maps representing the time delay of the time-varying blood flow at distinct body areas.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
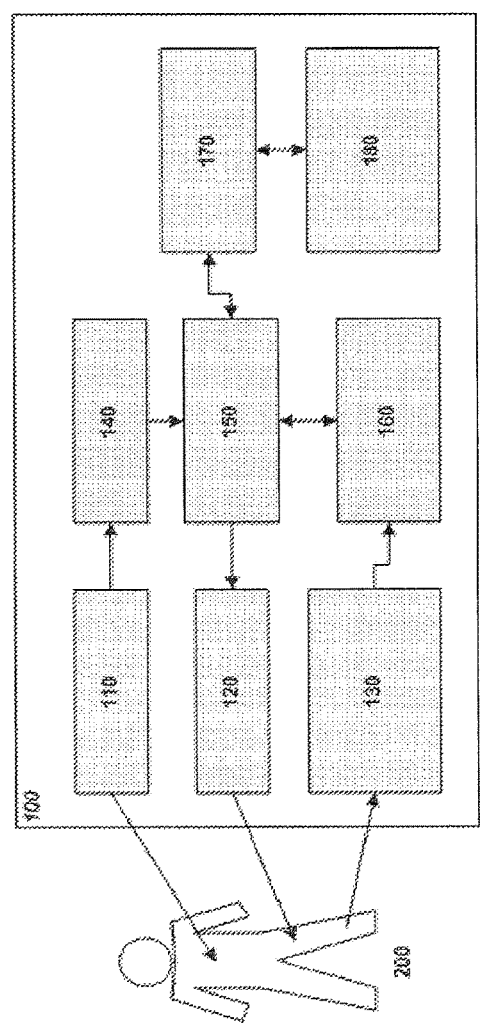
FIG. 1 a block diagram of the Functional Optical Coherent Imaging (fOCI) system platform according to a preferred embodiment of the invention.

FIG. 1 is a block diagram of the Functional Optical Coherent Imaging (fOCI) system platform according to a preferred embodiment of the invention for measuring microcirculation in response to stimulation and generating fOCI-maps of a subject 200. Therefore it is provided at least one Active Camera Unit ACU 110 and Image Processing Unit(s) IPU 140, a multi-modal Stimulation Unit(s) STU 120, and the Body Function Reference Measurement Unit(s) BFMU 130 monitoring the time course of preselected body parameters, all linked to a Central Clock and Processing Unit CCU 150, to which a Statistical Analysis Unit SAU 160 is attached for analyzing and monitoring hemodynamic and optical blood property response to the preplanned stimulation. This result is represented as at least one map for diagnosis and can be visualized on the Human Operator Interface HOI 170 which can be connected to a Picture Archiving and Communication System PACS 180.

Referring to FIG. 1, a general illustration of the Functional Optical Coherent Imaging (fOCI) system platform 100 is shown in accordance with the present invention.

In this general illustration, the fOCI system platform consists of the appropriate sub-units as:

The Active Camera Unit ACU 110, which contains the detector, optical means and an appropriate light source. It transmits the image data to the IPU 140 for further data processing.

The Stimulation Unit STU 120, which contains electrical, optical, mechanical, thermal and chemical means to stimulate a specific body function. The stimulation data and the monitoring data are transmitted to the CCU 150.

The Body Function Reference Measurement Unit BFMU 130, which detects and measures body functions, as for example heart beat cycle, breathing etc. These processed data are transmitted to CCU 150.

The Image Processing Unit IPU 140, which mainly receives the image data stream and processes the data. These processed data are transmitted to CCU 150.

The Central Clock and Processing Unit CCU 150, which ensures synchronized data acquisition and recording in order to provide a fully synchronized data set i.e. the image data from the ACU 110, the time-dependant stimulation data and the registered time dependant body function data for a statistical analysis.

The Statistical Analysis Unit SAU 160, which performs further data processing i.e. mainly the statistical data evaluation, and may result in fOCI maps. These processed data are transmitted to the HOI 170 and correspond to the final processed statistically enhanced images.

The Human Operator Interface HOI 170, which allows an operator to control the processes on the fOCI system platform, to view, manipulate and post-process the resulting data and images, as well as to interface the PACS 180

In a further step, the operator may archive the data set together with subject data in a fOCI attached memory or in a linked Picture Archiving & Communication System PACS 180. The subunits IPU 140, CCU 150 SAU 160, HOI 170 and PACS 180 can be incorporated partly or entirely into the same housing for ease of use.

The ACU 110 represents in a preferred embodiment of the invention a Laser Doppler System or a Laser Doppler Spectroscopic Imaging or a Laser Speckle Imager or an Optical Coherence Tomography system for the registration of images of the body area of interest. It is obvious that the fOCI platform, if equipped with several ACUs 110, can image different body areas of interests. The flow maps from different body areas of interest may show phase delays and thereby may contain diagnostically valuable information.

The ACU 110 may be understood as a generic camera system. It represents the optical information channel i.e. via an illumination source and a detection channel optical signal or images are registered or collected for further processing and extraction of meaningful diagnostic information. In addition, the ACU 110 contains a light source for coherent illumination in the case of a LDI and LSI, appropriate partial coherent light source(s) for OCT, and a multi-wavelength coherent source for LDSI.

Figure 2B:
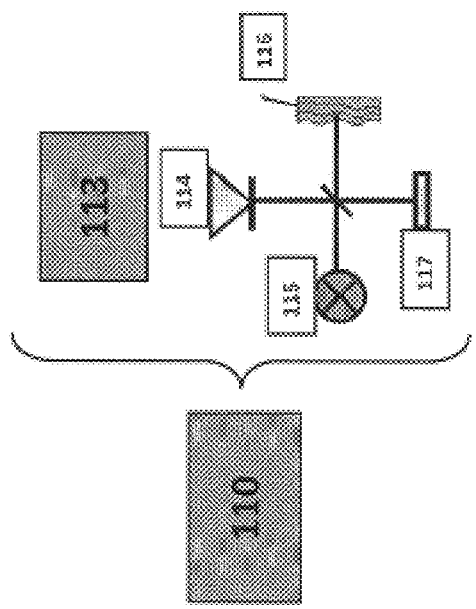
FIGS. 2A and 2B show block diagrams of the Active Camera Units ACU according to further preferred embodiments of the invention.
Figure 2A:
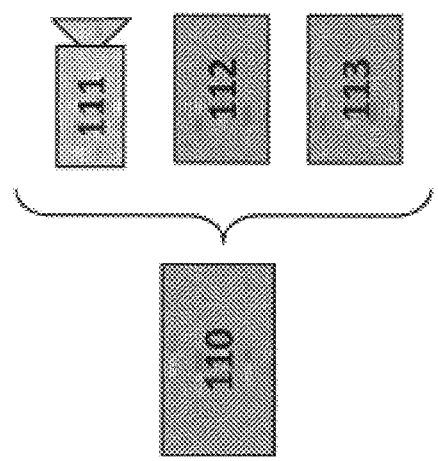

The block diagram of FIG. 2a specifies in more detail one ACU 110 containing a Laser Doppler System. For this specific realization, the ACU contains a light source or a laser source 112, a preferably fast camera system with optical means and optionally filtering means 111 which is preferentially a CMOS camera and appropriate control electronics 113 for steering the data communication and controlling the aforementioned subunits and for driving the image acquisition via the camera, the power regulation and off-on switching of the laser source and optionally a first step of image processing (for example in the case of Laser Doppler Imaging the calculation of perfusion, concentration or speed maps). This control electronics 113 ensures the fast data transmission to the IPU 140.

The block diagram shown in FIG. 2a shows basically a Laser Doppler System or a Laser Speckle System, Multi-Wavelength Laser Doppler Imaging or an ACU configured for fluorescence imaging appropriate by filtering means. The full disclosure and more configurations for these systems with all details are disclosed in the mentioned patents and in the cited literature.

FIG. 2b is a block diagram of the Active Camera Unit(s) ACU 110 comprising an Optical Coherence System/Tomograph as for example disclosed in detail for example in WO2007085992. The control electronics 113 steers and controls the interferometer system, which comprises a detector unit 114, an appropriate broadband source 115, and a reference mirror 117—all configured schematically to observe a sample or a subject 116. The full disclosure and more configurations and details are disclosed in the above mentioned patent application.

For this specific realization, the ACU contains the light source 115 which is preferentially a light source with a short coherence length, a fast detector 114 and the control electronics 113 for driving the image capture by the detector, the power regulation and off-on switching of the light source, scanning elements and the image processing. The control electronics 113 ensures the fast data transmission to the IPU 140.

Those skilled in the art will recognize that the STU 120 represents a generic stimulation unit. At least one stimulation channel will be used to send stimuli in a time-controlled manner to the subject. These emitted stimulus signals are of various types as for example an optical, acoustical, electrical, thermal or chemical signals, or images and/or pictures or representation of objects waiting naming or recognition by the subject.

A clear difference should be made between internal and external stimuli. An external stimulus can be an electric (voltage) signal to stimulate a particular part of the nervous system and in consequence an induced change in blood flow. An internal stimulus can be the subjects' own principal blood flow and its response observed in the body area of interest.

Figure 3:
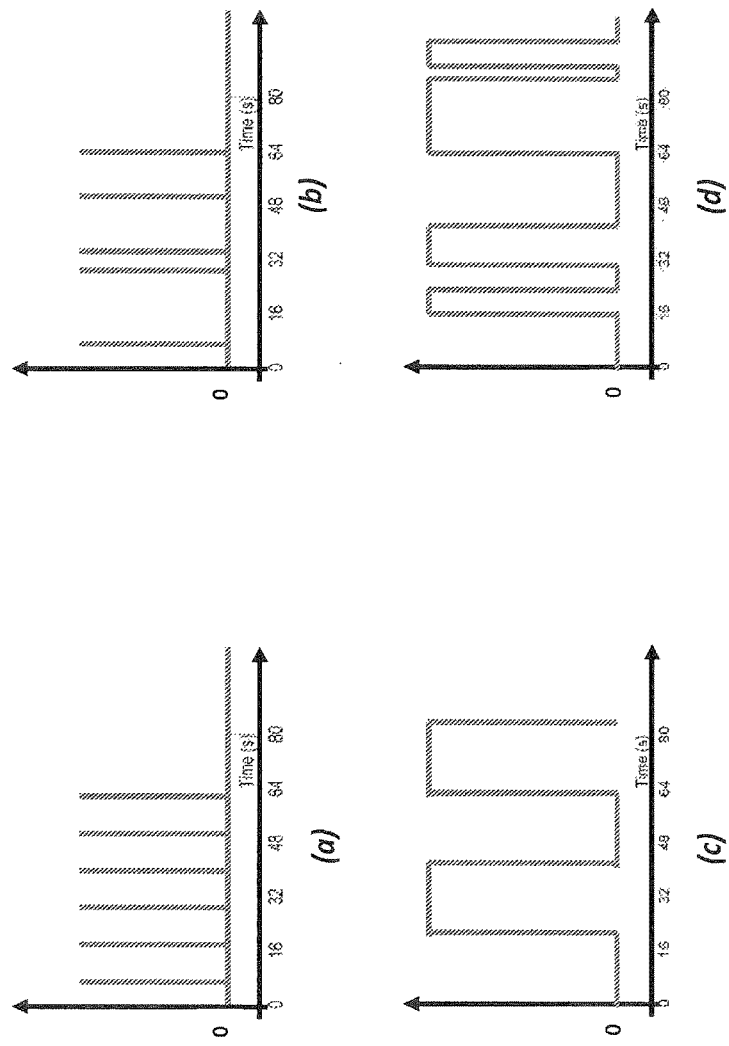
FIG. 3 shows typical stimulation patterns emitted by the STU to the subject.

FIG. 3 discloses typical stimulation patterns emitted by the STU 120 to the subject 200, which are realized by events of very short time either in a periodic or aperiodic train of events which may optionally vary in amplitude or stimulation patterns, which are realized in epochs of longer time duration either in a periodic or aperiodic train of epochs which may optionally vary in amplitude A typical stimulus sequence is organized as shown in FIG. 3. It may be advantageous to use a periodic or an aperiodic stimulus organized in events or epochs, where the stimulus is a short event, an impulse (shorter than the typical blood flow response) or lasting during the total epoch i.e. a time interval during the total stimulus "on" time. Finally, these stimulation events and/or epochs result in an induced general stimuli response resulting in a blood flow change which is captured by the "optical observation channel", the ACU 110.

The BFMU 130 monitors body functions as for example heart beat, breathing, myogenic or neurogenic activities, but not limited to these activities. The main purpose of the BFMU is the monitoring of subject reactions which may overlay the signal of interest.

Figure 4:
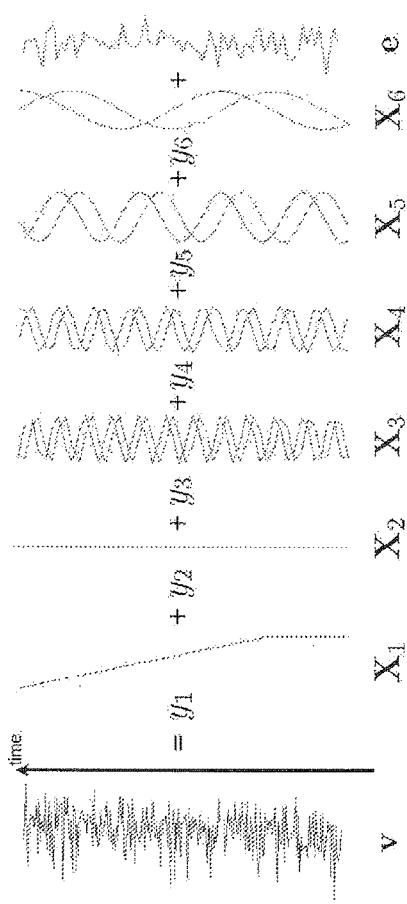
FIG. 4 shows and visualizes a typical example of a linear regression analysis.

A typical example of this situation is shown in FIG. 4 which shows and visualizes a typical example of a linear regression analysis. The measured signal per pixel over time is decomposed into several regressors Xi i.e. signal contributions which add up including the residual noise contribution to the raw signal v. this means that in this example a measured signal v is explained by a general linear model as a sum of signal $X_1$ (the signal of interest), signal $X_2$ (a baseline), signal $X_3$ (the heartbeat), signal $X_4$ (breathing), signal $X_5$ and $X_6$ (myogenic or neurogenic activities) and e, the residual, which is mainly a residual noise component. In this particular example measured with ACU 110 containing a Laser Doppler Imaging system, the signal v represents the intensity time course of one pixel. The signal $X_1$ is heavily distorted by a sum of $X_2 \ldots X_6$ of respective blood flow contributions—the signal v was captured by the ACU 110, whereas the blood flow contributions $X_3 \ldots X_6$ are measured and monitored by the BMFU 130. The contributions $X_1$, $X_2$ are extracted by an appropriate algorithm and represent the functional response deduced across the observation channel ACU 110 and the body function parameters measured by the BMFU 130.

The image processing unit IPU 140 receives raw or preprocessed image data from one or more ACUs 110 each consisting of one or more data channels. The IPU processes these data and sends the results to the CCU 150. In addition, the resulting images and flow maps are labeled with metadata such as the current ACU 110 settings and the time of acquisition (received from the CCU 150) required by the SAU 160.

Figure 5:
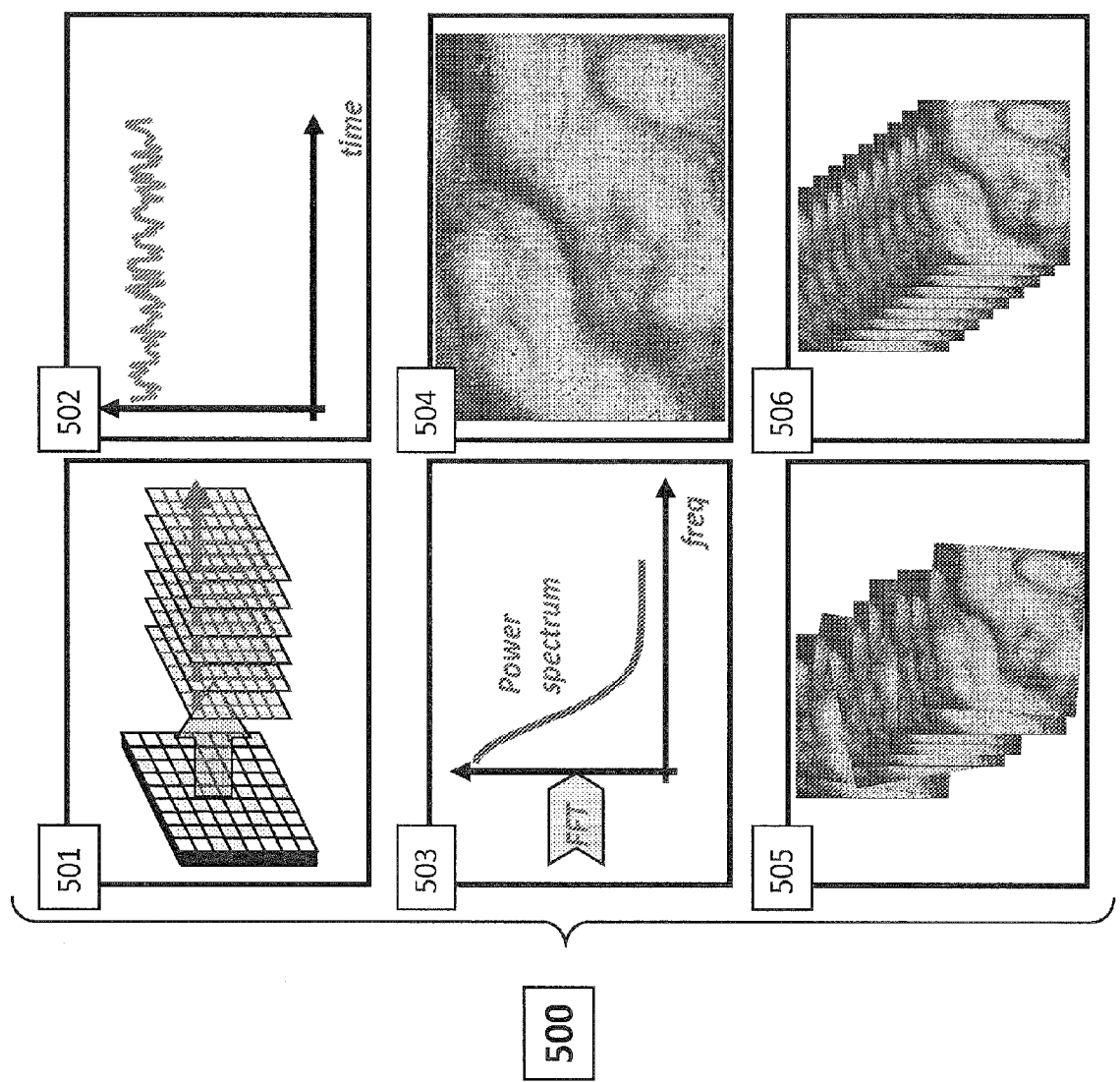
FIG. 5 shows and visualizes the process steps performed in the Image Processing Unit IPU according to one embodiment of the invention.

FIG. 5 shows and visualizes the process steps performed in the Image Processing Unit IPU 140. Step 141 until step 144 indicates all image processing steps for a classical LDI image processing procedure. After the image acquisition (image raw data per pixel) a typical stack at these images is memorized at high speed and arranged for temporal Fourier analysis 142. The Fourier transform allows a simple filtering as well as the calculation of the power spectrum and a moment analysis 143 which yields finally a concentration, perfusion and via the ratio a speed map, all together so-called flow maps. Overall this leads to an important data reduction if the initially raw data are compared with the final flow map. These flows are again memorized, optional realigned in translation, rotation and magnification distortions 145 before finally being transferred to the CCU and SAU 146 for the statistical analysis.

With an ACU 110 based on Laser Doppler Imaging, the IPU 140 allows amongst other things, the reconstruction of information (see FIG. 5) such as:
    photographic images, which can be optionally used for autofocus purposes,
    perfusion, concentration and velocity maps for each wavelength by applying algorithms such as the momentum analysis, or any combination this information such as absorption maps which can be described as the ratio of two perfusion maps acquired over the same area of interest at the same time but with different wavelengths.

With an ACU 110 based on Laser Speckle Imaging, the IPU 140 can reconstruct photographic information and velocity maps. With an ACU 110 based on Optical Coherence Tomography, the IPU 140 reconstructs the spatial information.

As shown in the steps 145 and 146 on FIG. 5, all these IPUs 140 may include any combination and any algorithm for the rearrangement of pixels, realignment and co-registration steps as well as filtering. Images and maps may be compressed with algorithms such as those defined by the Joint Photographic Experts Group (JPEG).

The central clock & processing unit CCU 150 serves as the central hub for acquiring and merging data arriving from STU 120, BFMU 130 and IPU 140. In addition, it serves as time master and allows the data arriving from STU 120, BFMU 130 and IPU 140 to be labeled with a synchronized time, which is required by the SAU 160 to which the merged data is send and from which the resulting data are received.

The CCU 150 also provides the HOI 170 with a central interface for controlling and communicating with the fOCI system platform components STU 120, BFMU 130 and IPU 140.

Figure 6:
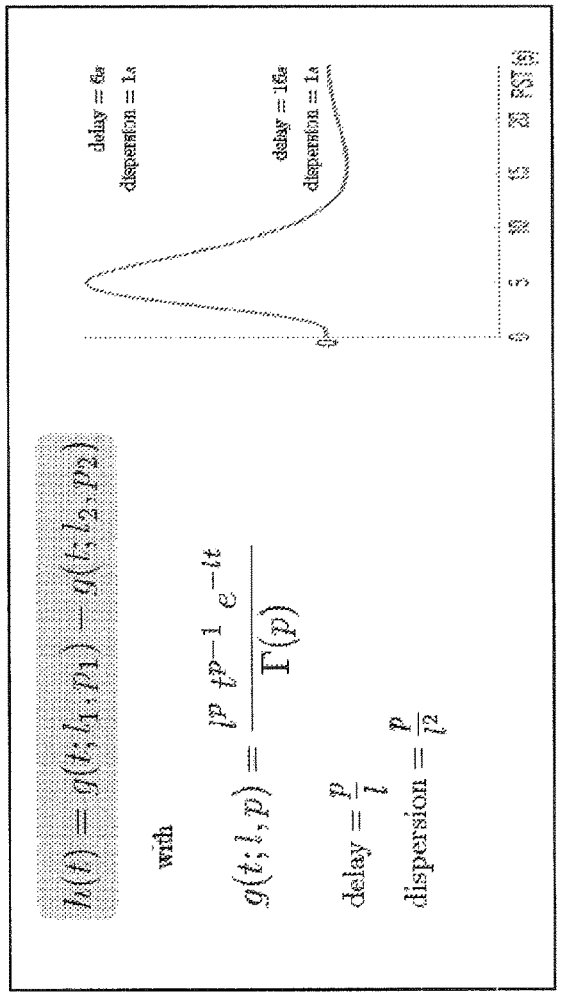
FIG. 6 shows a hemodynamic model equivalent to models used in fMRI.

The statistical analysis unit SAU 160 receives synchronized data from the CCU 150. These synchronized data packages represent the pre-processed data i.e. the flow maps from the ACU 110 and IPU 140 units, the synchronized data from the STU 120 and the monitored and synchronized data from the BFMU 130. The stimulation data arriving from the CCU 150 and shown in FIG. 3 are further processed as for example by a convolution with an appropriate hemodynamic model as shown in FIG. 6. For those skilled in the art, this algorithm and modeling is based on a known hemodynamic response function as those used in functional MRI imaging. Here, we use the difference of two Gamma functions, for which the chosen parameters for the delay parameter and the dispersion values are examples for the measurements chosen and in no cases restricted to the disclosed processes. So far, this model has proved to be useful and appropriate for a fOCI process. This disclosed hemodynamic model is in no case the only possible way to model hemodynamic response convoluted with periodic or aperiodic events or epochs used for stimuli. This hemodynamic response function is used for building together with the stimulation pattern the stimulation regressor.

For those skilled in the art, there are more models known in the scientific literature, which may be used for modeling the hemodynamic response.

Figure 7:
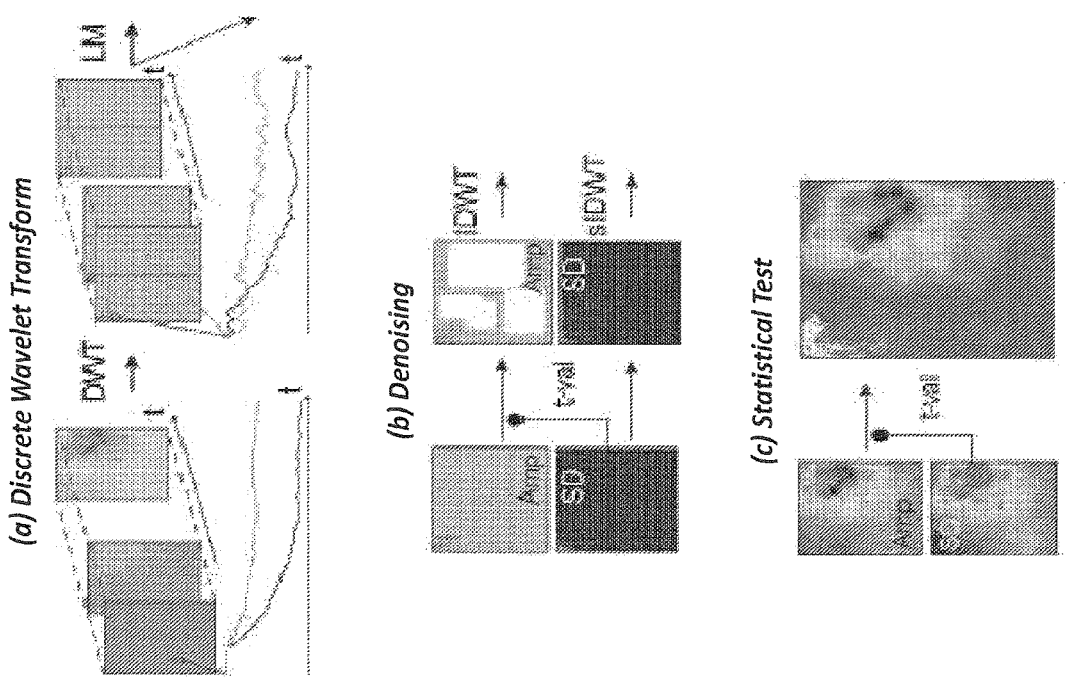
FIG. 7 shows an advanced statistical analysis according to another embodiment of the invention.

FIG. 7 shows an advanced statistical analysis, decomposed into 3 major steps:

1. Instead of only a pixel-wise regression analysis, the flow maps (perfusion, concentration or speed) undergo first a discrete wavelet transform before the following linear regression analysis based on the wavelet transforms. This statistical analysis (for example the Students t-test) with an appropriate contrast definition leads to an activation parameter uw and the corresponding standard deviation of uw at each wavelet location.

2. The wavelet-transformed data are filtered by an adaptive threshold procedure, rejecting the noise contributions and leading to a further data reduction and smoothing. This processing step finishes with an inverse wavelet transform into the original x-y space.

3. The final statistical test including an optional Bonferoni correction leads to the fOCI-maps showing the alpha-test values (the hypothesis testing based on the t-Test) as final result of induced changes of microcirculation due to stimuli.

This represents a highly innovative step above the classical flow maps of optical image techniques. fOCI takes into account the flow maps, but enhances the information content in these images based on statistical tests.

As shown in FIG. 7, the flow maps are further processed by a spatial transform that compacts the energy of the flow map(s), for example the discrete wavelet transform (FIG. 7a);

fitting a regression model—preferentially a linear regression model—to each of these transform coefficients (FIG. 7a);

extracting a parameter of-interest (contrast), which may consist of a linear combination of regressor weights but not limited thereto (FIG. 7a);

a general denoising concept, which may be realized by an adaptive thresholding in the transform domain or an equivalent filtering for suppressing the noise contributions (FIG. 7b);

a corresponding inverse spatial transform (FIG. 7b);

and a final statistical testing at a desired confidence level, optionally including Bonferoni correction; the procedure takes into account the denoising in the transform domain and compensates for multiple comparisons (FIG. 7c).

The final information is presented as the extracted contrast represented in a functional map, the so-called fOCI map, which may be overlaid with a conventional digital image or digitized photo. Any other combination with independently acquired functional or anatomical images as fMRI or PET or x-ray or ultrasound imaging is also possible. The calculated functional map possesses now diagnostic data with statistical significance, due to the statistical testing based on a high number of degrees of freedom as well as on the spatial transform (i.e., wavelet analysis), the denoising or filtering, which all result in a significant enhancement of statistical confidence in the extracted data for recovering evidence of the (modeled) hemodynamic response caused by the prior stimulation of the subject.

For those skilled in the art it is evident that many of these processes have to be calculated per pixel or transform coefficient. The overall evaluation and calculation process can be greatly accelerated by massively parallel and/or dedicated computation which can be realized on FPGA or ASIC technologies but is not limited thereto.

Summarizing, the total data processing for the SAU 160 as indicated in FIG. 7 takes full advantage of transforming the flow data by an appropriate spatial transform (in this case the spatial wavelet transform), by using linear algorithms to obtain at least one parameter of interest, to perform a denoising procedure, to retransform the data from the wavelet domain back to the spatial domain by an inverse wavelet transform and to extract the final functional data based on suitable statistical testing. Similar calculations have been published, but not applied to optical imaging methods. The publications "Van De Ville D., Seghier M. L., Lazeyras F., Blu T., Unser M., NeuroImage, vol. 37, no. 4, pp. 1205-1217, Oct. 1, 2007"; "Van De Ville D., Blu T., Unser M., NeuroImage, vol. 23, no. 4, pp. 1472-1485, December 2004" and "Van De Ville D., Blu T., Unser. M., IEEE Engineering in Medicine and Biology Magazine, vol. 25, no. 2, pp. 65-78, March-April 2006" contain a thorough demonstration of these principles and techniques. The SAU 120 can also give feedback to the operator by a measure for the goodness-of-fit of the general linear model.

Several ACUs 110 together with their corresponding IPUs 140 can be combined to a whole body area network which offers the unique possibility to observe and to analyze phase delays of blood flow between the different observation nodes, which opens a wide range of applications. To observe very large surface areas, combining multiple cameras can become an interesting option. Even more so, multiple cameras distributed at various areas of interest over a body make it possible to study phase delays between the nodes of the multi-node phase array. The crucial synchronization between the ACU/IPU pairs is ensured by the CCU 150.

The human operator interface HOI 170 connects to the CCU 150 and the PACS 180 and is a combination of software and hardware, typically in the form of a personal computer, which has three purposes:

The first purpose is to allow the operator to control the processes on the fOCI system platform. Among other tasks, this may include configuring the area of interest, starting and stopping the ACUs 110, choosing the information to reconstruct in the IPU 140, defining or selecting the stimulation signal in the STU 120, and defining the parameters for the SAU 160. Controlling the safety measures of the fOCI platform such as Laser safety also makes part of the HOI 170.

The second purpose is to display and visualize the acquired images, maps and data so that they can be viewed, interpreted and manipulated by the operator. The HOI 170 can also assist the operator by providing diagnostic suggestions.

The third purpose is to make the data persistent and to associate them to subjects and sessions. This can be either achieved directly by the HOI 170 or by a connected PACS 180. The HOI 170 and the PACS 180 can operate in the same housing. Interfacing with third party software such as MatLab from MathWorks, Inc. also forms part of the HOI 170.

Picture archiving and communication systems PACS 180 are computers or networks dedicated to the storage, retrieval, distribution and presentation of images. The medical images can be stored in a standard format such as the DICOM (Digital Imaging and Communications in Medicine) format.

The purpose of a PACS 180 in a fOCI system platform consists of making the acquired images persistent and accessible for later use both by the HOI 170 as well as by third party software. It can provide a single point of access for images and their associated data (i.e. it should support multiple modalities) as well as an interface of the fOCI system platform with existing hospital information systems HIS.

Particular attention is necessary for multi-wavelength or spectral broadband illumination. As is well known by those skilled in the art, various bio-molecules participating in the metabolism have specific molecular signatures, which are measurable and/or accessible by various spectroscopic methods exist, which find an extension in imaging. As an example we would like to mention absorption spectroscopy with its counterpart in imaging, where the specific absorption spectra and absorbance of a substance can be used to image local variations of concentrations of these bio-molecules, the so-called absorbants. Similar arguments apply for reflectance or fluorescence. In addition, the fluorescence response can be measured or in the fluorescence intensity, or in a ratio measurement at different wavelengths or by accessing the lifetime response of these specific fluorescent molecules or bio-molecules with a specific fluorescent marker.

Particular attention should be drawn to the oxy-deoxyhemoglobin ratio measured at different wavelengths and the possibility to image this important metabolic parameter with high sensitivity using the fOCI platform. For oxy-deoxyhemoglobin ratio imaging, an absorption image at about 800 nm wavelength, where the oxy- and deoxy-hemoglobin absorption are equal (isobestic point), is related to an absorption image at about 700 nm wavelength, where the deoxyhemoglobin absorption is about one order of magnitude stronger than the oxy-hemoglobin absorption. This oxy-deoxy-hemoglobin ratio can be used for metabolic imaging based on the following relations:

At each pixel, the measured absorption $A(\lambda)$ is given as $$A(\lambda) = C_{oxy} \cdot A_{oxy}(\lambda) + C_{deoxy} \cdot A_{deoxy}(\lambda) = C_{hemoglobin} \cdot (Poxy \cdot A_{oxy}(\lambda) + [(1-P)]oxy) \cdot A_{deoxy}(\lambda))$$

where $C_{hemoglobin}$ is the hemoglobin concentration, Poxy the fraction of oxy-hemoglobin and $A(\lambda)$ the absorption at the illumination wavelength $\lambda$. At the isobestic point, $A_{oxy} = A_{deoxy}$ and $A = C_{hemoglobin} \cdot A_{isobestic}$.

Taking the absorption measurement at 700 nm into account, the parameter of interest Poxy can be extracted from the ratio:

$$\frac{A(700 \text{ nm})}{A(800 \text{ nm})} = P_{oxy} \frac{A_{oxy}(700 \text{ nm}) - A_{deoxy}(700 \text{ nm})}{A_{isobestic}} + \frac{A_{deoxy}(700 \text{ nm})}{A_{isobestic}}$$

Figure 8:
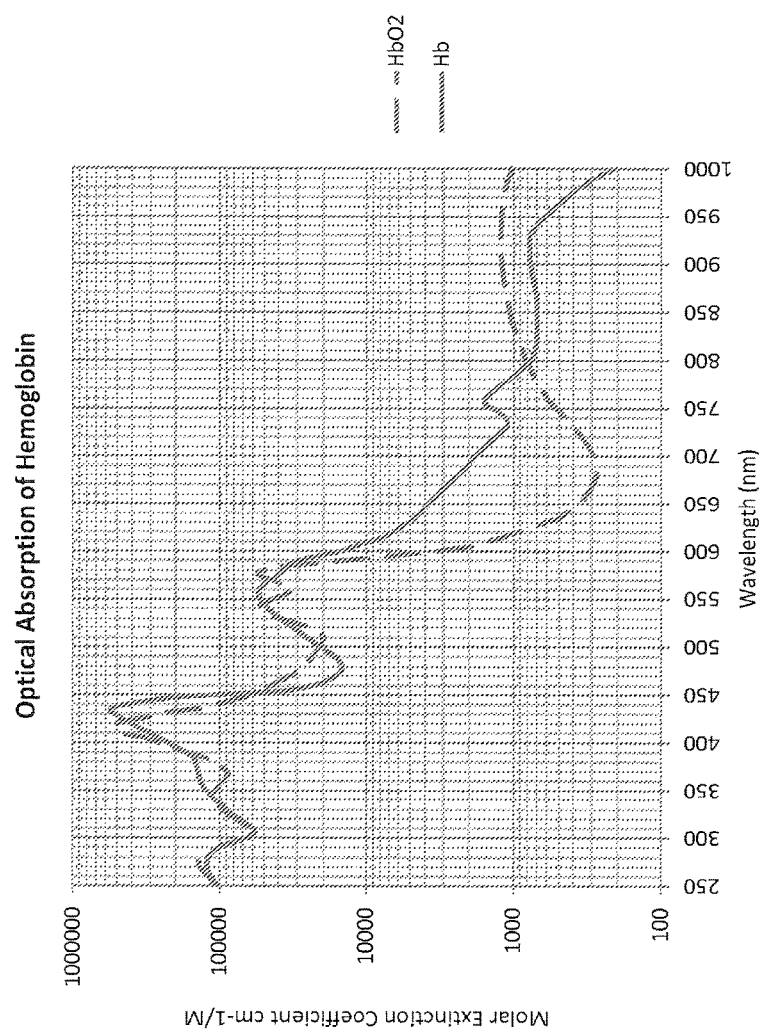
FIG. 8 shows an absorption spectrum of oxy-hemoglobin (HbO2) and deoxy-hemoglobin (Hb)

Regardless of the fact that the absorption values differ approximately by an order of magnitude and as indicated in FIG. 8, the deoxy-oxygen ratio is often difficult to measure in a controlled manner, for instance because the measured absorption stems from the hemoglobin and all other substances present at the measured location.

FIG. 8 is showing an absorption spectrum of oxy-hemoglobin (HbO2) and deoxy-hemoglobin (Hb) and in particular the so-called isobestic point at approx. 800 nm in contrast to the high difference of the molar extinction coefficient at 680 nm. (from http://omlc.ogi.edu/spectra/hemoglobin/—data compiled by Scott Prahl, 1998).

However, limiting this ratio-measurement of the flowing blood cells by a two-wavelength optical coherent flow imaging modality such as LDI gives this ratio-measurement together with the concentration, i.e. the statistically analyzed zero moment of the filtered signal as disclosed in this patent, and thus a reliable metabolic image with high diagnostic value.

This example is only a clear description and disclosure of potential concepts for deoxy-oxygen ratio imaging. Other wavelength choices or ratio formulae are possible and will in no case represent improvements to the disclosed innovative height. The absorption or ratio measurement by itself is known to those skilled in the art, but the image contrast enhancement in combination with LDI imaging and improved reliability due to the statistical analysis as disclosed in the fOCI process are further improvements of high diagnostic value.

Beyond deoxy-oxygen ratio imaging further metabolic agents can be accessed based on the various spectroscopic imaging modalities. However, as in the case for deoxy-oxygen ratio imaging, these metabolic processes can be imaged with improved confidence if based on the disclosed fOCI process.

Blood is a complex liquid containing many different molecules which may originate from the subject's metabolism or may be injected or given as a drug to the subject. If these molecules show fluorescence as intrinsic fluorescence, also known as auto-fluorescence or extrinsic fluorescence by a specific labeling with a fluorophore (added by a specifically labeled antibody) fluorescent images can be acquired. As known by those skilled in the art these fluorescent images display the concentration of specific molecules in the bloodstream and can be acquired simultaneously with the concentration and perfusion maps. Combining the concentration or perfusion data with the specific molecular concentration information based on the fluorescent images adds multi-modal images with enhanced information to the fOCI-platform. For those skilled in the art, fluorescence images can be acquired based on intensity or lifetime in the frequency domain or the time domain. All these different image acquisition modes are included in the more general description of fluorescence imaging. An appropriate ACU is based on the described camera with a more appropriate filter element of appropriate illumination and acquisition means.

Figure 9:
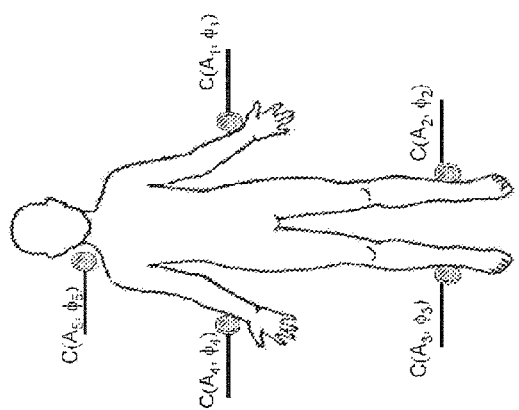
FIG. 9 shows a whole body area network for measuring phase delays between the different body areas of interest according to one embodiment of the invention.

FIG. 9 shows a whole body area network for measuring phase delays between the different body areas of interest. C(Ai,fi) represents the ACU-IPU combination with the individual data transmission to the CCU for further data processing.

Several ACUs 110, together with their corresponding IPUs 140 can be combined in a whole body area network, which offers the unique opportunity to observe and analyze phase delays of blood flow between the different observation nodes, which opens a wide range of applications in particular for medical diagnosis. To observe very large surface areas, combining multiple cameras can become an interesting option. Even more so, multiple cameras distributed at various areas of interest of the body as indicated in FIG. 9 enable the study of phase delays between the nodes. Simultaneous recording from all ACU/IPU pairs is crucial for this type of measurement and, as disclosed in the fOCI process, is ensured by the CCU 150. As shown in FIG. 9, active camera units ACU 110 in a whole body area network may contain different types of optical coherent imaging modalities, such as Laser Doppler Imaging, Laser Speckle Imaging or Optical Coherence Tomography, but not limited to them.

It is known to those skilled in the art, that the systolic arterial pressure, i.e. the peak pressure in the arteries, arrives at different times if measured at body areas of interest with varying distances from the heart. This blood flow delay, or phase delay, can be distorted due to pathologies, physical efforts, drugs or stimulations and may indicate a dysfunction of the subject. For those skilled in the art there are various ways to precisely determine the blood flow delay between different observation nodes as for example indicated in FIG. 9.

The phase delays can be determined by cross-correlating the raw data acquired at the different observation nodes. An appropriate filtering may be added to enhance the signal to noise ratio and the robustness of the algorithm. Performing the cross-correlation based on Fourier transforms will not represent a novelty for those skilled in the art. A diagnostic value would be the cross correlation coefficients deduced from raw images between the different observation nodes, optionally combined with the variances i.e. related to the max-min ratio over the time-varying signal. This diagnostic value can be further improved if baseline values are established over a representative subject group of healthy subjects.

The phase delays between different observation nodes can also be determined based on the regression analysis, which can be used to extract the specific heart beat component (the heart beat regressor) at the corresponding body areas of interest. This is indicated in FIG. 4 as well as in the explanations concerning the BFMU. The regression analysis represents an alternative way for phase and amplitude extraction, which can be determined a posteriori from the recorded flow maps.

Figure 10:
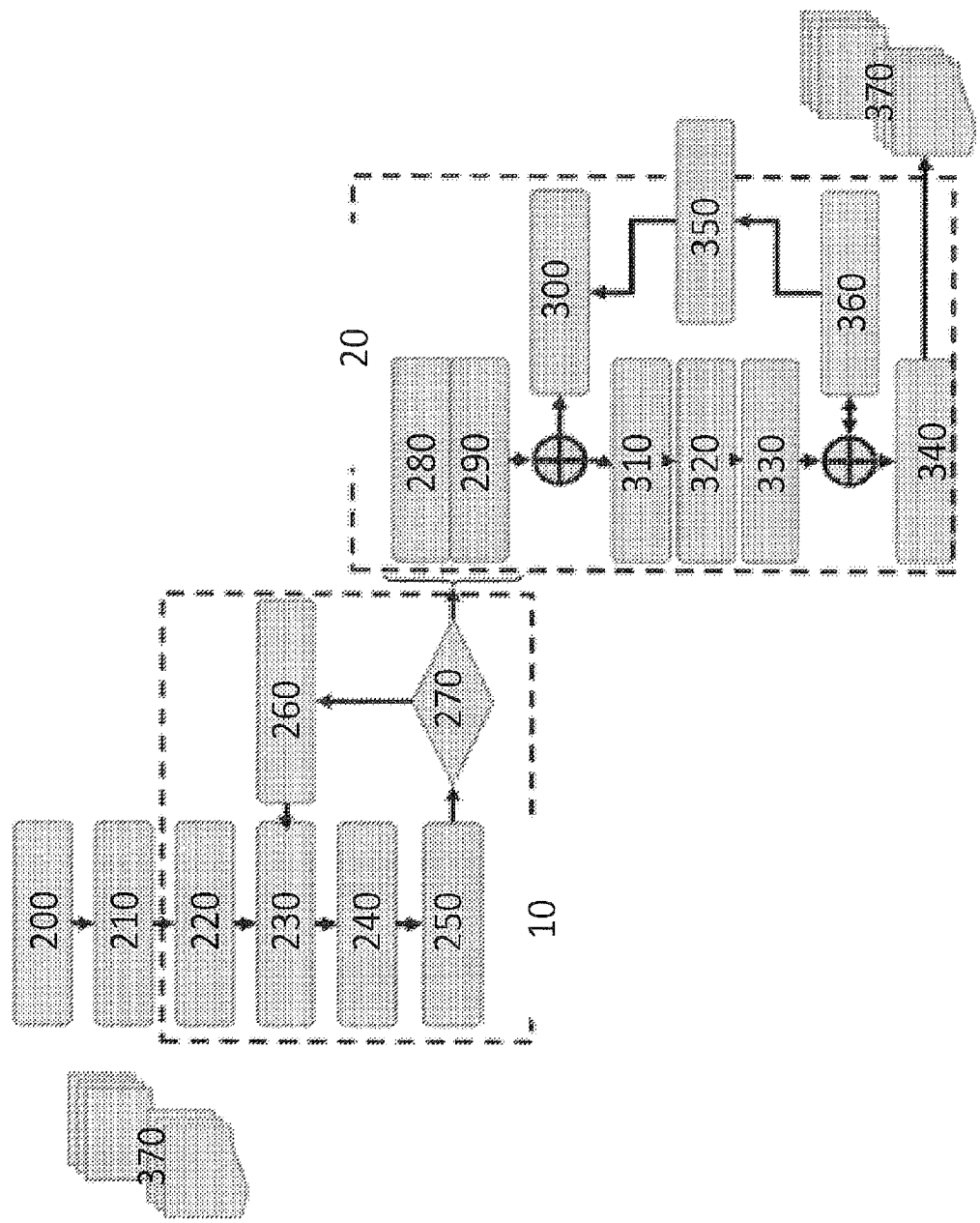
FIG. 10 shows a process flow chart of the fOCI process according to another embodiment of the invention.

FIG. 10 shows a process flow chart of the fOCI process. The diagrams shows the principal sub-division into a first sub-process (set-up phase) mainly for an optimized subject positioning followed by the final sub-process (examination phase). During this final sub-process the raw data are acquired, processed for flow maps and finally processed for the fOCI maps. The clinical advice may lead to an additional examination phase for complementary diagnostic, differential diagnostics and/or an optimization procedure.

The fOCI-examination process comprises several steps, as shown in FIG. 10. In the set-up phase 10 after the start of the application 200, the operator is asked to enter the subject's identification information 210. The operator then selects a first stimulation profile 220 appropriate to the subject and the examination to be done. The following steps are basically the subject preparation. After linking the BFMU and the STU by an operator a proper subject positioning 230 is done in addition to verification of a proper alignment and a control of the proper functioning of the fOCI platform. The positioning of the ACUs for imaging the selected area of interest 250 is part of this set-up phase. Further body functions are engaged and acquired 240. This set-up phase may include a repositioning 260 with repeated control 270 of all BFMU channels and image acquisitions of the ACUs. If all preparation requirements are met the operator can proceed to the examination phase 20.

This examination phase 20 comprises the acquisition of all signals relevant to the BFMU channels 280, the image acquisition by the ACUs 290 and the stimuli 300 by the STU. During these examination steps the flow maps 310 are shown at the HOI. After ending the stimulation profile a statistical analysis 320 can be performed. The resultant fOCI maps combined with the medical/scientific advice is the diagnostic result 340. The operator may by checking fOCI maps 330 decide to add/modify the stimulation profile 350, add medical opinion/advice 360 or even to add/modify additional BFMU channels or ACUs in order to complement or optimize the diagnostic information. All this information is displayed on the HOI and is as the final step of the examination phase transferred to the PACS/HIS system 370.

Figures 11A, 11B:
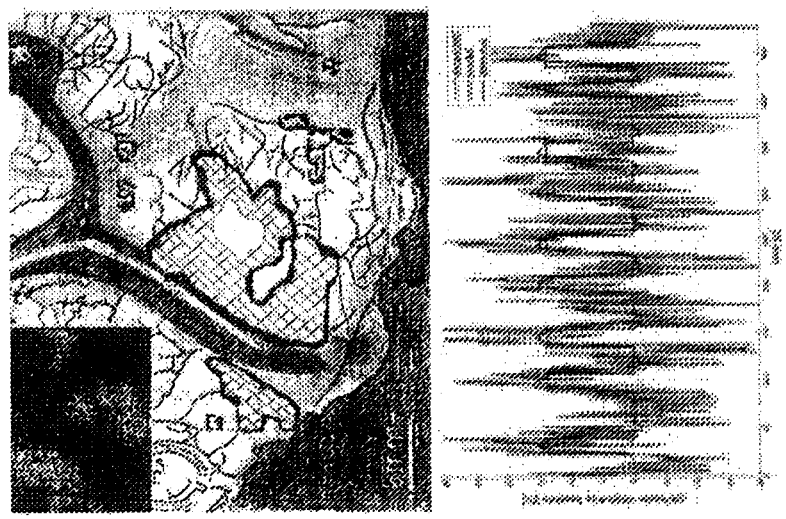
FIG. 11a shows a fOCI map according to one embodiment of the invention.
FIG. 11b shows the average time course of the activated region after subtracting unrelated regressors according to one embodiment of the invention.

FIG. 11a shows a fOCI map i.e. the result of the statistical analysis of the main response to the activation. The squared region shows the activated region of the brain and the white region therein shows the strongly activated region of the brain. The result of the statistical analysis has been cross-checked with a fMRI measurement (see FIG. 12). As can be seen both results correlate very well with the data obtained by optical measurement.

Figure 12:
FIG. 12 shows the site of the operation identified by electro-stimulation as being responsible for the stimuli for comparison with the results according to the invention as well as the fMRI image (inset).

FIG. 11b shows the average time course of the activated region (t-value above 7.5) after subtracting unrelated regressors, also the aperiodic epochs, their convolution with the hemodynamic function for task-related signal and the stimulus function FIG. 12 shows the site of the operation identified by electro-stimulation as being responsible for the stimuli i.e. finger tapping (encircled area 'A'), the inset is a Mercator MRI representation with fMRI activation regions (in white) obtained during finger tapping; the tumor, to the upper right, has compressed the hand-knob area (upper left of 'A') such that the fMRI signal obtained during finger tapping has been split. The fOCI map based on optical imaging (LDI Imaging) shows an identical cerebral activation zone when compared with the fMRI functional images.

According to the invention there are many possible and meaningful ways of use of a Functional optical coherent imaging platform, for instance in human medical applications.

In particular the fOCI platform can be used in neurosurgery and in particular for optical functional imaging during surgery, in dentistry, diabetes, wound healing, ulcers, burns, transplant and bypass surgery, reperfusion, plastic surgery, skin grafting and grafting bed diagnosis, angiology, in particular hypo- and hypertension, neurology and brain research, diagnosis for multiple sclerosis, oncology, ophthalmology and in particular glaucoma follow-up, and/or cosmetics, reconstructive and cosmetic surgery.

Other advantageous uses comprise all medical diagnosis related to the microcirculation system and pathological dysfunctions.

Further to that the Functional optical coherent imaging platform according to the invention can be used for generating fOCI maps in animal imaging applications such as animal and pathology diagnosis, vitality testing, veterinary diagnosis and/or in all veterinary diagnosis related to the animal microcirculation system and pathological dysfunctions.

In industrial applications concerning flow management, in particular heat flow, liquid and gas cooling and electronics and cooling circuitry the fOCI platform can also be used. Further applications could be ink and dye flows as well as particles or colloid suspension flow.

Other applications for the inventive functional optical coherent imaging platform include safety and security applications as well as agricultural application such nutrient flow in plants, testing of maturity.

What is claimed is:

1. A functional optical coherent imaging (fOCI) device comprising:
    an active camera unit (ACU) connected to an image processing unit (IPU) for calculating a hemodynamic flow map using the coherence properties of a coherent and/or partially coherent light source at a selected body area of interest of a subject;
    a stimulation unit (STU) for applying an external or detecting an internal stimulation pattern of the subject;
    a central clock and processing unit (CCU), with interconnections to the ACU and the IPU for collecting the blood flow map from the IPU and the stimulation pattern from the STU; in a timely synchronized manner;
    a post-processing unit (statistical analysis unit, SAU) suitable for statistical analysis of the received synchronized data from the CCU, configured to calculate a functional OCI (fOCI) map which represents a statistical confidence map of the hemodynamic response caused by the stimulation pattern; and
    a screen to display the fOCI map.

2. The device of claim 1 further comprising a body function reference unit (BFMU), which detects and measures body functions that are physiological processes that happen without any internal or external stimulus, connected to the CCU, and the SUI further configured to remove signals representative of the reference date received from the BFMU from the signal of interest received from the ACU before and during application of an internal or external stimulus.

3. The device of claim 1 wherein the screen further displays the hemodynamic flow map.

4. The device of claim 1 wherein the IPU uses Laser Doppler imaging for calculating the hemodynamic flow map.

5. The device of claim 1 wherein the IPU uses Laser Speckle imaging for calculating the hemodynamic flow map.

6. The device of claim 1 wherein the SAU uses regression analysis.

7. The device of claim 1 wherein the SAU uses a wavelet transform.

8. A method for acquiring a functional optical coherent (fOCI) map comprising the steps of:
    applying an external stimulation pattern or detecting an internal stimulation pattern from a subject;
    acquiring a series of hemodynamic flow maps using optical coherent imaging in a timely synchronized manner with the stimulation pattern;
    generating a confidence map of the hemodynamic response caused by the stimulation pattern by statistically analyzing the synchronized hemodynamic flow map and the stimulation pattern;
    detecting a body function reference signal and using the detected signal to remove signals representative of the body function from the hemodynamic flow map or from the confidence map; and
    displaying the confidence map.

9. The method from claim 8 wherein the acquisition of the hemodynamic flow map is done using Laser Doppler Imaging.

10. The method from claim 8 wherein the acquisition of the hemodynamic flow map is done using Laser Speckle Imaging.

11. The method from claim 8 wherein the generation of the confidence map includes performing a regression analysis.

12. The method from claim 8 wherein the generation of the confidence map includes performing a wavelet transform.

* * * * *